United States Patent [19]

Kratky et al.

[11] Patent Number: 5,008,381

[45] Date of Patent: Apr. 16, 1991

[54] SELECTIVE CLEAVAGE OF NARINGIN

[75] Inventors: Zdenek Kratky, New Milford; John S. Tandy, Litchfield, both of Conn.

[73] Assignee: Nestec S.A., Vevey, Switzerland

[21] Appl. No.: 483,879

[22] Filed: Feb. 23, 1990

Related U.S. Application Data

[63] Continuation-in-part of Ser. No. 116,555, Nov. 3, 1987, abandoned.

[51] Int. Cl.$^5$ .................... C07H 1/00; C07H 1/08
[52] U.S. Cl. ........................ 536/8; 536/4.1; 536/18.1; 536/18.2; 536/18.5; 536/124
[58] Field of Search ............ 536/4.1, 18.1, 18.2, 536/8, 124, 18.5

[56] References Cited

U.S. PATENT DOCUMENTS

| | | | |
|---|---|---|---|
| 2,510,797 | 6/1950 | Burdick et al. | 536/8 |
| 2,700,047 | 1/1955 | Wilson | 536/8 |
| 2,744,893 | 5/1956 | Wender et al. | 536/8 |
| 2,780,620 | 2/1957 | Krider et al. | 536/6.3 |
| 2,950,974 | 8/1960 | Smythe et al. | 536/8 |
| 4,067,748 | 1/1978 | Rowe | 536/124 |
| 4,238,483 | 12/1980 | Frazier | 536/8 |
| 4,297,348 | 10/1981 | Frazier | 536/8 |
| 4,339,442 | 7/1982 | Takemoto et al. | 536/4.1 |
| 4,428,876 | 1/1984 | Iwamura | 536/4.1 |
| 4,772,334 | 9/1988 | Hatanaka et al. | 536/124 |

OTHER PUBLICATIONS

Mizelle et al.; Analytical Biochemistry 12(2): 316–324, Aug. 1965.
Pulley et al.; J. Amer. Chem. Soc. 61: 175–176 (1939).

*Primary Examiner*—Ronald W. Griffin
*Assistant Examiner*—Nancy S. Carson
*Attorney, Agent, or Firm*—Vogt & O'Donnell

[57] ABSTRACT

Naringin is selectively cleaved into L-rhamnose and naringenin-t-7-glucoside by heating naringin in solution under particular conditions of acid hydrolysis. Upon cooling the reaction medium, a liquid phase containing L-rhamnose and a semi-solid phase containing naringenin-7-O-glucoside are obtained from which those compounds may be isolated.

20 Claims, No Drawings

SELECTIVE CLEAVAGE OF NARINGIN

CROSS REFERENCE TO RELATED APPLICATION

This application is a continuation-in-part application of application Ser. No. 07/116,555 filed Nov. 3, 1987.

BACKGROUND OF THE INVENTION

The present invention relates to a process for hydrolysis of naringin by means of an acid catalyst.

Naringin, which is present in grapefruit and obtained readily from grapefruit canning wastes, has the chemical formula:

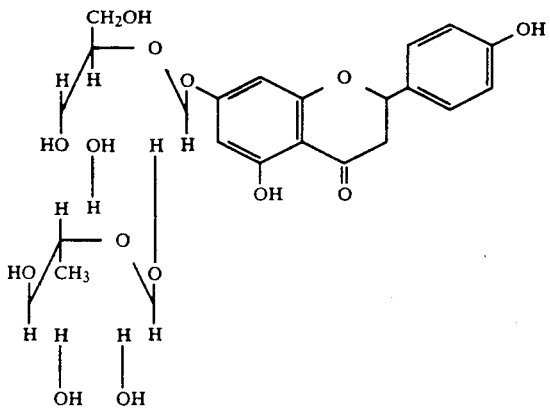

L-rhamnose, which has sweetening properties but provides little caloric content to humans because it is not metabolized readily by the body and which may be employed as a precursor for preparation of flavoring compositions, has the chemical formula:

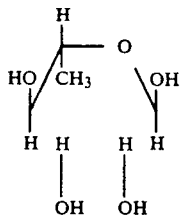

L-rhamnose is present in its free form in poison ivy and is contained in some polysaccharides of microbial origin, in some mucilages and in some plant exudates and is a constituent moiety of many glucosides, e.g., quercitrin, rutin and naringin. Prior methods to isolate and obtain useful quantities L-rhamnose involve processing steps which are not practical and economically feasible for industrial production.

Illustrative of a process for obtaining L-rhamnose from naringin is described by G. N. Pulley, et al., "Preparation of Rhamnose from Naringin", J. Amer. Chem. Soc., 61, p. 175 (1939), in which naringin is hydrolyzed by refluxing it with sulphuric acid (~3.7%). Glucose, L-rhamnose, naringenin and other reaction products are formed by the reaction. The reaction medium is cooled and naringenin, which is semi-solid, is separated from the cooled reaction medium. The remaining filtrate then is neutralized and heated to boiling in the presence of charcoal. The charcoal treated product is concentrated in vacuo and then is inoculated with yeast to ferment glucose. L-rhamnose is isolated from the fermented liquor by several steps of concentration in vacuo and washing.

Moreover, efforts in the art have not provided a means for treating naringin such that one might readily obtain not only L-rhamnose but also obtain naringenin-7-O-glucoside, which is useful as a starting material for the synthesis of various chemicals and pharmaceuticals, particularly capillary dilatory agents, and which has the chemical formula:

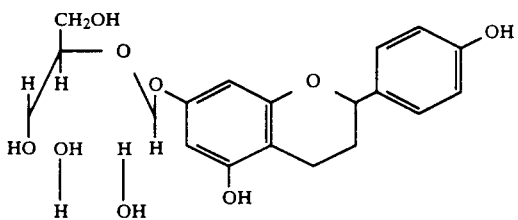

SUMMARY OF THE INVENTION

We have discovered that the O-glycosidic linkage which connects the glucose moiety of the naringin molecule to the naringenin moiety of the naringin molecule is more acid stable than the O-glycosidic linkage which connects the L-rhamnose moiety to the naringenin-7-O-glucoside moiety which is a combination of the glucose and naringenin moieties. Thus, the present invention provides a process for cleaving naringin to obtain not only L-rhamnose but also naringenin-7-O-glucoside by a simple and efficient method.

Accordingly, although quantitative determinations of the binding force and energy necessary to selectively cleave naringin as contemplated by the present invention are not known to applicants, the present invention is characterized in that naringin in aqueous solution is heated in agitated contact with a hydrolyzing agent, an acidic catalyst, which provides $H^+$ ions to naringin molecules in an amount sufficient for cleaving the O-glycosidic linkage of the naringin molecule which connects the naringin molecule L-rhamnose and naringenin-7-O-glucoside moieties while substantially avoiding cleaving the naringin molecule O-glycosidic linkage which connects the naringin molecule glucose and naringenin moieties and thereby forming a liquid reaction medium containing rhamnose and naringenin-7-O-glucoside.

After selectively hydrolyzing the naringin, the reaction medium is cooled for a time sufficient to form a liquid phase and a semi-solid phase. The phases then are separated. L-rhamnose is isolated from the liquid phase and naringenin-7-O-glucoside is isolated from the semi-solid phase, each of which may be accomplished readily by crystallization procedures.

In one specific embodiment, the present invention comprises selectively cleaving naringin into L-rhamnose and naringenin-7-O-glucoside by heating naringin in aqueous solution in agitated contact with a strong cationic exchange resin. In further embodiments, the present invention comprises heating and agitating a reaction medium of naringin and an acid in aqueous solution under conditions of acid molarity sufficient and at a temperature and time sufficient for hydrolyzing and selectively cleaving the naringin into substantially only L-rhamnose and naringenin-7-O-glucoside moieties.

DETAILED DESCRIPTION OF THE INVENTION

As is known in the art, naringin is dissolved best in heated water. An aqueous solution of naringin heated to a temperature of about 100° C. may contain, depending upon the pH of the solution medium, naringin in an amount of up to about 30-35% by weight based upon the weight of the solution. Above that range of amounts, the solution becomes saturated with naringin. In the practice of the present invention, for reasons of efficiency and productivity, it is preferred that the amount of naringin employed be that amount which results in an aqueous solution of naringin approaching, under the pH and temperature conditions to be employed in the hydrolysis reaction, its limit of solubility, although lesser amounts may be employed.

In carrying out the process of the present invention, generally, it is preferred that naringin first be added to and dispersed in water, and it is not required that all of the desired reaction amount of naringin be in solution while heating to the desired reaction temperature. Thus, the acid catalyst may be added before or during heating the naringin solution/suspension to the desired reaction temperature, or in the case of, particularly, a strong cationic exchange resin, the resin may be first contacted with the heated naringin reaction solution at the reaction temperature.

Whether employing an acid as the catalyst or employing a strong cationic exchange resin as the catalyst, the naringin solution reaction medium is agitated during the reaction, which is believed primarily to provide a favorable effect upon the kinetics of the reaction. The terms "agitation" and "agitated contact" in the context of this invention mean that the naringin reaction medium is subjected to at least some movement. The extent of agitation is not critical and may be effected by stirring, or by pumping, or in the case of a packed resin column, by passing the naringin solution through the column for efficient contact with the resin.

In carrying out the present invention, strong cationic exchange resins have been found to be particularly useful because, in general, removing the resin from the reaction medium is simpler than removing acid from the reaction medium. Strong cationic exchange resins suitable for the present invention are exemplified by those which have sulfonic acid, or an equivalent thereof, as a functional group, as is well-known to those skilled in the art. Examples of such resins are DOWEX-50W, DOWEX-HCR-W-2, AMBERLITE-IRA-118H, AM-BERLITE-IR-120-PLUS, AM-BERLITE-IR-122 and AMBERLITE-IR-130, for example.

To carry out the reaction with a strong cationic exchange resin, the reaction may be performed batchwise wherein the resin simply is added to and suspended in the naringin solution/suspension. In such cases, the reaction medium having the resin in suspension then is agitated to obtain efficient contact during the reaction. As referred to above, it also is possible for the naringin, preferably in solution, to be passed through a heated column packed with the resin which would provide the necessary agitation and contact.

The amount of strong cationic exchange resin employed to contact the naringin solution reaction medium may range from an amount of from about 5 g to 200 g per 1 of the naringin solution to be reacted. For any given amount of naringin, the lesser the amount of resin and its contact surface, or the lesser the extent of agitation, the longer the time of reaction and/or the higher the reaction temperature may be. Preferably, the resin is employed in an amount of from 10 g to 100 g per 1 of naringin solution to be reacted.

When operating with a strong cationic exchange resin as the catalytic hydrolyzing agent, it has been found that temperatures and times of the reaction do not have a critical effect upon the reaction and the desired results of selective cleavage of naringin into L-rhamnose and naringenin-7-O-glucoside. What affects the reaction the most is the amount of resin employed and the extent of agitation for contacting the resin with the naringin solution. Thus, employing a resin enables the desired reaction to proceed without substantial cleavage of the O-glycosidic linkage between the glucose and naringenin moities and without the formation of substantial undesired degradation products. Thus, the hydrolysis reaction may be carried out to its desired completion at temperatures above room temperature and generally at temperatures of from about 70° C. to about 200° C., and hence, under reflux conditions, for a time sufficient, as further discussed below, to complete the reaction.

Although the procedures of obtaining the desired products by the hydrolysis reaction of naringin with an aqueous acid catalyst medium are simple when carried out in accordance with the present invention, control of the reaction amounts and conditions so that the naringin is cleaved selectively is, particularly with some acids as discussed further below, more critical. As a general rule, the concentration and relative strength of the acid employed is the critical parameter in enabling one to obtain the desired selective cleaving of naringin. Thus, also as a general rule, acids known to the artisan as weak acids may be employed in higher concentrations together with higher reaction temperatures and longer reaction times than are the case with acids known to the artisan as strong acids which, in comparison, must be employed in lesser concentrations together with generally lower reaction temperatures and shorter times.

The most preferred acids employed in the hydrolysis reaction of the present invention, because they allow broad ranges of reaction temperatures and times but still substantially avoid undesired hydrolysis of the naringin molecule and undesired degradation products, are hydrochloric acid and trifluoroacetic acid. These acids may be employed as a benchmark for determining amounts and conditions employed with other acids.

In the case of hydrochloric acid, it is essential that the concentration of the acid in the naringin solution being reacted does not exceed about 0.1 M. That is, it has been discovered that even though L-rhamnose and possibly some naringenin-7-O-glucoside may be formed and obtained in acidic reaction solutions having a greater molarity and hence, a greater concentration of acid, other undesired hydrolysis and or degradation products are formed without regard to reaction temperatures and times. Thus, if one operates with solutions having a hydrochloric acid concentration of greater than about 0.1 M in the naringin solution, further isolation and purification procedures, such as employed in the prior art, are required just to obtain rhamnose. Preferably, the concentration of hydrochloric acid ranges from about 0.03 M to about 0.075 M in the naringin solution. Optimum results are obtained with hydrochloric acid having a concentration of about 0.05 M, for example, from about 0.045 M to about 0.055 M.

In the case of trifluoroacetic acid, which is art recognized as a weaker acid than hydrochloric acid, it is essential that the concentration not exceed about 0.2 M in the naringin solution, and preferably trifluoroacetic acid will be employed at a concentration of from about 0.08 M to about 0.18 M in the naringin solution, with optimum results being obtained with a concentration of about 0.125 M to about 0.135 M.

As with the strong cationic resins, the hydrolysis reaction carried out with hydrochloric acid and trifluoroacetic acid may be performed at a temperature above room temperature and preferably at temperatures of from about 70° C. to about 200° C., and hence, the reaction may be carried out under reflux conditions for a time sufficient to complete the reaction, as further discussed below.

Likewise, when employing acids weaker than hydrochloric and trifluoroacetic acids, such as acetic and trichloroacetic acids, concentrations of such acids somewhat in excess of about 0.2 M may be employed and generally longer times and/or higher reaction temperatures may be employed to obtain the desired results, but the selective hydrolysis is best achieved at lower concentrations which have a molarity which does not exceed about 0.2 M and by what may be deemed "mild" conditions.

With acids stronger than hydrochloric acid, to obtain the desired selective cleavage and avoid obtaining undesired hydrolysis and decomposition products from the naringin molecule, one should proceed with lesser concentrations of such acids, with milder reaction conditions and generally shorter reaction times as compared with the concentrations and conditions employed with hydrochloric acid. Thus, with multivalent strong acids, such as sulphuric and phosphoric acids, lower concentrations, i.e., less than 0.05 M, and generally, milder reaction conditions of temperature and time advisedly are employed. Illustrative of caveats which must be considered with strong acids is that we have found that with sulfuric acid if reflux temperatures are employed, i.e., about 100° C. and above, even at low concentrations, for example, 0.025 M, the naringin usually will be hydrolyzed into naringenin, L-rhamnose and D-glucose, and generally, partial decomposition of naringenin will occur. Thus, advisedly, reaction temperatures of 100° C. and above are not employed with such strong acids.

Thus, the desired selective cleaving of the O-glycoside linkage of naringin to provide L-rhamnose and naringenin-7-O-glucoside is sensitive to, most critically, the nature of the acid and the concentration of acid employed. Therefore, to obtain the results disclosed herein, the conditions of time and temperature which also will affect the selectivity of the cleaving reaction and which, together with agitation, which affects principally the kinetics of the reaction, may be manipulated with respect to the nature of the acid employed and its concentration, which, by reason of the guidance provided herein, may be determined and varied readily by one of ordinary skill.

Depending upon the concentration of the acid or the amount of resin employed, and depending upon the temperature employed, the desired results may be obtained in anywhere from a reaction time of from about 5 secs to about 6 hrs. In general, the reaction is carried out for from about 1 min to about 2 hrs.

Further, it has been found that operating with an apparatus such as one in which the naringin to be reacted is passed through a tube and contacted and heated by injecting steam in the tube, a procedure known in the art and to the artisan generally as UHT or ultrahigh temperature processing, provides not only the desired agitation by intimate contact of the reactants, but also because of the temperatures generated, i.e., from 120° C. to about 170° C., but also enables efficient processing at the low end of the time ranges noted above. Likewise, such conditions may be employed for apparatus known the the art as plate heat exchangers.

After the hydrolysis reaction, in the case of employing a cationic exchange resin in a batch-type system wherein the resin is agitated with the naringin reaction medium, the resin most efficiently is removed from the reaction medium prior to cooling. In the case of the reaction being effected with an acid, the acid is removed as discussed below.

After the hydrolysis reaction, whether the reaction medium has been separated from a resin or contains acid, the reaction medium is cooled to a temperature of from about 0° C. to about 30° C. and left to stand and allow phase separation of a liquid phase and a semi-solid phase which generally will occur within about at least 1 hour. Longer times may be employed to assure complete separation. Upon phase separation, the liquid phase then is separated physically from the semi-solid phase, such as by decantation, although filtering may be employed. L-rhamnose then may be isolated from the liquid phase and naringenin-7-O-glucoside may be isolated from the semi-solid phase by crystallization techniques.

Preferably, the liquid phase is treated with active carbon to decolorize the product, and the carbon will also remove impurities. Such is conveniently performed by adding the active carbon to the liquid phase in an amount of about 0.1% to about 0.5% by weight based upon the weight of the liquid and by heating to a temperature such as 70° C. to 110° C. and agitating the liquid medium.

After filtering the active carbon treated liquid, the liquid is concentrated, preferably by subjecting it to conditions of vacuum. Preferably, during the concentration step, the liquid is agitated, preferably with bubbling of air or other gas, such as an inert gas, through the liquid which, in the case of the liquid phase containing acid, assists in stripping and evaporating acid from the liquid. The resultant concentrated liquid generally has a syrupy consistency.

Note should be made that relatively volatile acids such as hydrochloric and trifluoroacetic acid will evaporate readily during the vacuum treatment. However, if strong mineral acids such as sulphuric acid are employed in the reaction, such are not volatile and will tend to concentrate during the vacuum treatment. Hence, further removal steps, which also could be employed with the more volatile acids, although generally not required, generally desirably are employed. Such removal steps include neutralizing the liquid phase with bases such as alkaline earth metal hydroxides, particularly calcium hydroxide and barium hydroxide, prior to concentrating the liquid phase. By reason of neutralization, insoluble salts form and the liquid phase is separated from the salts by decantation, filtration, or by other conventional means. Additionally, to remove the acid, the liquid phase conveniently may be passed through or contacted with an anion exchange resin.

After concentrating the liquid, L-rhamnose may be obtained from the syrup simply by seeding the concentrated liquid with crystals of L-rhamnose and allowing the L-rhamnose to crystallize from the concentrated liquid.

Naringenin-7-O-glucoside may be obtained from the semi-solid sediment phase simply by allowing the sediment to stand in water and crystallize. Preferably, the water is slightly acidified.

EXAMPLES

The following examples further illustrate the present invention. Percentages are by weight unless otherwise indicated.

EXAMPLE 1

200 g of naringin are added to 600 ml of water. Some of the naringin dissolves and some remains in suspension. 6 ml of trifluoroacetic acid are added to the suspension which provides a molarity of about 0.13 M. The acidified suspension then is refluxed for 1 hour with constant stirring with a magnetic stirrer during which time all of the naringin dissolves into solution. The reaction medium then is cooled overnight at 4° C. which provides a supernatant liquid phase lying above a semi-solid phase.

The supernatant liquid and semi-solid phases are separated by decantation. The supernatant liquid phase is treated with 1 g of active carbon, filtered and treated in vacuo to concentrate the liquid while bubbling a stream of air through the liquid which assists in removing residual trifluoroacetic acid. The resulting syrup is seeded with a few crystals of L-rhamnose and allowed to crystallize at room temperature. 32 g of L-rhamnose is obtained.

EXAMPLE 2

The procedure described in Example 1 is followed except that, instead of 6 ml of trifluoroacetic acid, 3 ml of 10 N hydrochloric acid is used which provides a molarity of about 0.05 M. The amount of L-rhamnose obtained is 30 g.

COMPARISON EXAMPLE

The procedures of Examples 1 and 2 are followed except that 18 ml of 10 N hydrochloric acid is used which provides a molarity of about 0.3 M. After the hydrolysis reaction, liquid supernatant and semi-solid phases form. The supernatant phase is separated from the semi-solid phase by decantation. The separated supernatant phase is found to have free glucose in an amount corresponding to about 60% of the theoretical yield should naringin be cleaved at each of its O-glycosidic linkages. Because of the presence of glucose in the supernatant phase, isolation of rhamnose by simple crystallization was not deemed feasible and thus was not attempted.

EXAMPLE 3

100 g naringin and 25 g of AMBERLITE-IRA-118H (H+ form) ion exchange resin (5 weight %) are added to 500 ml of water and the resulting suspension is refluxed for 2 hours with stirring by a magnetic stirrer during which time all of the naringin dissolves into solution.

The ion exchange resin is separated from the reaction medium by filtration at 100° C. and the filtrate is cooled to 2° C. and allowed to stand in a reaction flask for 2 days during which time a supernatant liquid phase forms above a syrupy sediment phase.

The supernatant liquid phase is separated from the sediment by decantation, treated with 1 g of active carbon, filtered and concentrated into a semi-solid as in Example 1. The semi-solid then is seeded with crystalline L-rhamnose. 12 g of L-rhamnose are obtained from a first crystallization and an additional 6 g of L-rhamnose is obtained from the mother liquor.

The sediment obtained from the reaction medium is treated to isolate naringenin-7-O-glucoside by dissolving 2 grams of the sediment in 5 ml of methyl alcohol. That solution is introduced in a column packed with 200 g of silica gel 60 (FLUKA). The column is eluted with a solvent of acetone and methyl alcohol in a ratio of 10:1 and the resulting fractions are collected.

The fractions containing naringenin-7-O-glucoside are pooled and concentrated, and 1 g of naringenin-7-O-glucoside is obtained.

EXAMPLE 4

500 g of naringin is suspended in 10 l of water to which 50 ml of concentrated hydrochloric acid is added. The suspension is pumped through a (UHT) high temperature short time system as described above wherein the solution is passed through a tube and contacted with steam. The suspension is treated at about 151° C. and is retained in the system for about 1 min. The treated suspension is allowed to stand and cool, and a supernatant liquid and a semi-solid sediment forms.

The supernatant liquid is separated from the sediment and is neutralized by the addition of a strong anion exchanger in −OH form. The neutral supernatant liquid then is concentrated under a vacuum while bubbling air through the liquid. The concentrated mass then is seeded with crystalline L-rhamnose. 87 g of L-rhamnose is obtained.

EXAMPLE 5

The procedure of Example 4 is repeated but instead of treating the supernatant phase, the semi-solid sediment phase is treated by allowing the sediment to stand in 2.5 l of water acidified with 5 ml of hydrochloric acid. White crystals appear on the surface of the semi-solid sediment after several days of standing. The crystals are allowed to grow until substantially all the sediment is converted into crystalline material suspended in a liquid. The crystals are separated from the liquid by filtration and then dried. Naringenin-7-O-glucoside comprises about 80% by weight dried material.

From the foregoing, it will be apparent to one of ordinary skill that various apparatus, conditions and parameters may be employed for practicing this invention and for obtaining the results of the present discovery without departing from the spirit and scope of the invention as defined by the following claims.

EXHIBIT A
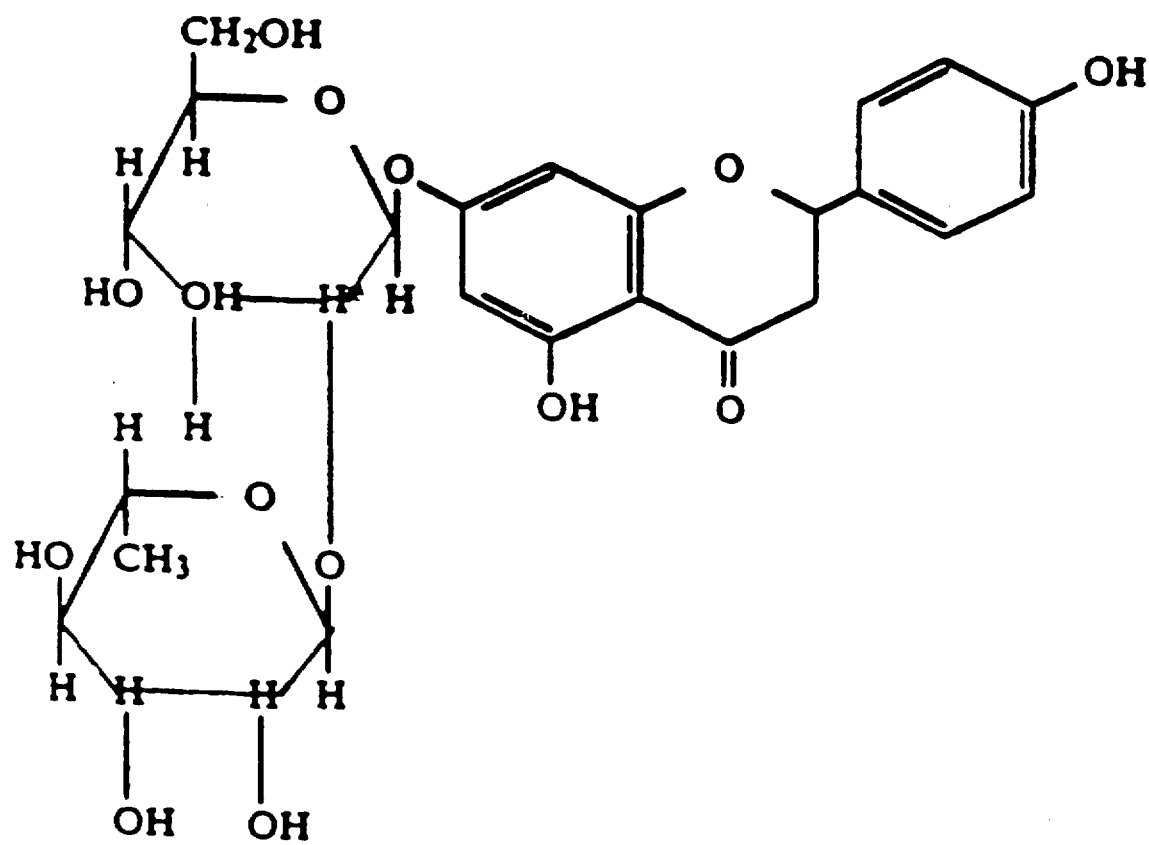

EXHIBIT B
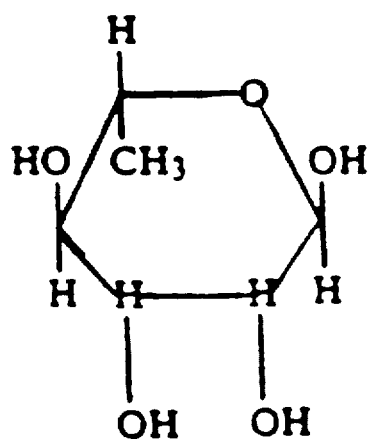

EXHIBIT C
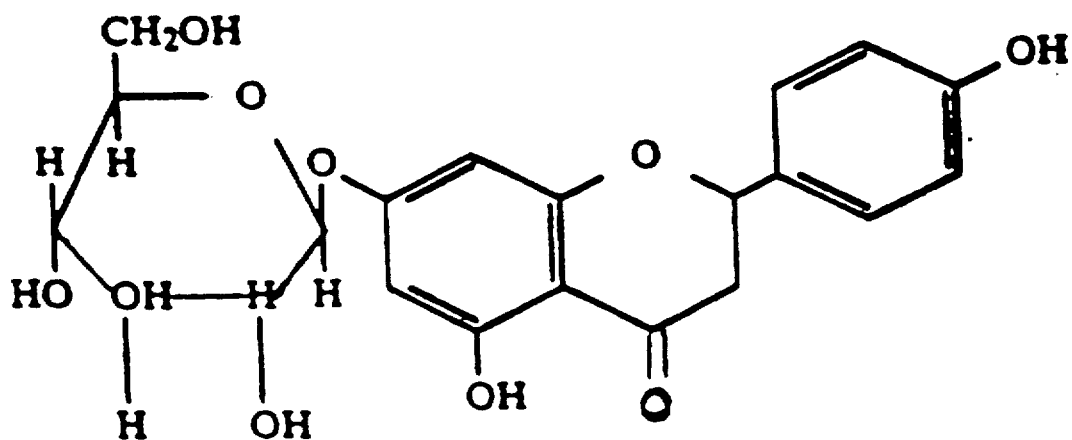

We claim:

1. A process for treating naringin for obtaining L-rhamnose and naringenin-7-O-glucoside comprising:
   heating naringin in aqueous solution in agitated contact with an acidic catalyst in an amount sufficient for providing H+ ions to naringin molecules for cleaving the O-glycosidic linkage of the naringin molecule which connects the naringin molecule L-rhamnose and naringenin-7-O-glucoside moieties while substantially avoiding cleaving the naringin molecule O-glucosidic linkage which connects the naringin molecule glucose and naringenin moieties and thereby forming a liquid reaction medium;

cooling the liquid reaction medium to form a liquid phase and a semi-solid phase;

separating the liquid phase from the semi-solid phase; and isolating L-rhamnose from the liquid phase and isolating naringenin-7-O-glucoside from the semi-solid phase.

2. A process according to claim 1 wherein L-rhamnose is isolated by concentrating the liquid phase to obtain a concentrated liquid and then by seeding the concentrated liquid with crystals of L-rhamnose and allowing L-rhamnose to crystallize from the concentrated liquid.

3. A process according to claim 2 wherein the liquid phase is concentrated under conditions of vacuum.

4. A process according to claim 1 wherein the naringenin-7-O-glucoside is isolated by adding water to the semi-solid phase and allowing naringenin-7-O-glucoside to crystallize from the semi-solid phase.

5. A process according to claim 1 wherein the acidic catalyst is a strong cationic exchange resin.

6. A process according to claim 5 wherein the resin is in an amount for agitated contact with the naringin, of from about 5 g to 200 g per l of the naringin solution.

7. A process according to claim 1 wherein the acidic catalyst is an acid selected from a group consisting of hydrochloric acid having a molarity in the naringin solution which does not exceed about 0.1 M and trifluoroacetic acid having a molarity in the naringin solution which does not exceed about 0.2 M.

8. A process according to claim 7 wherein the molarity of the hydrochloric acid is from about 0.03 M to about 0.075 M and the molarity of the trifluoroacetic acid is from about 0.08 M to about 0.18 M.

9. A process according to claim 5 or 7 wherein the naringin solution is heated in agitated contact with the acidic catalyst to a temperature of from about 70° C. to about 200° C.

10. A process according to claim 9 wherein the naringin solution is heated in agitated contact with the acidic catalyst for from about 5 sec to about 6 hr.

11. A process according to claim 1 wherein the acid catalyst is an acid selected from a group consisting of acetic acid and trichloroacetic acid.

12. A process according to claim 11 wherein the acid has a molarity which does not exceed about 0.2 M.

13. A process according to claim 1 wherein the acidic catalyst is an acid selected from a group consisting of sulfuric acid and phosphoric acid which has a molarity which does not exceed about 0.05 M and wherein the naringin solution is heated in agitated contact with the acidic catalyst at a temperature below 100° C.

14. A process according to claim 1 wherein the acidic catalyst is an acid and wherein the naringin solution and acid are passed through a tube and contacted with steam for providing agitated contact and heating.

15. A process for treating naringin for obtaining L-rhamnose comprising:

heating naringin in aqueous solution to a temperature of from about 70° C. to 200° C. in agitated contact with an acid catalyst selected from a group consisting of a strong cationic exchange resin, hydrochloric acid having a molarity in the naringin solution which does not exceed about 0.1 M and trifluoroacetic acid having a molarity in the naringin solution which does not exceed about 0.2 M for from about 5 secs to 6 hrs for forming a reaction medium containing L-rhamnose and naringenin-7-O-glucoside;

cooling the liquid reaction medium to form a liquid phase and a semi-solid phase;

separating the liquid phase from the semi-solid phase; and isolating L-rhamnose from the liquid phase.

16. A process according to claim 15 wherein the L-rhamnose is isolated by concentrating the liquid phase to obtain a concentrated liquid and then by seeding the concentrated liquid with crystals of L-rhamnose and allowing L-rhamnose to crystallize from the concentrated liquid.

17. A process according to claim 16 wherein the liquid phase is concentrated under conditions of vacuum.

18. A process according to claim 15 wherein the acid catalyst is a strong cationic exchange resin and the resin is in an amount for agitated contact with the naringin, of from about 5 g to 200 g per l of the naringin solution.

19. A process according to claim 15 wherein the acid catalyst is hydrochloric acid and the molarity of the hydrochloric acid is from about 0.03 M to about 0.075 M.

20. A process according to claim 15 wherein the acid catalyst is trifluoroacetic acid and the molarity of the trifluoroacetic acid is from about 0.08 M to about 0.18 M.

* * * * *

UNITED STATES PATENT AND TRADEMARK OFFICE
CERTIFICATE OF CORRECTION

PATENT NO. : 5,008,381
DATED : April 16, 1991
INVENTOR(S) : Zdenek Kratky, et al It is certified that error appears in the above-identified patent and that said Letters Patent is hereby corrected as shown below:

In the ABSTRACT, line 2, "naringenin-t-7-glucoside" should be --naringenin-7-O-glucoside--.

The formula at column 1, lines 16-32 should be deleted, to appear as per attached Exhibit A.

The formula at column 1, lines 38-47 should be deleted, to appear as per the attached Exhibit B.

Column 1, line 67, "in vacuo" should be italicized.

Column 2, line 1, "in vacuo" should be italicized.

The formula at column 2, lines 10-20 should be deleted, to appear as per the attached Exhibit C.

Column 3, line 51, "AM-BERLITE-IR-122" should be --AMBERLITE-IR-122--.

Column 7, lines 26-27, "in vacuo" should be italicized.

Signed and Sealed this

Twenty-second Day of September, 1992

Attest:

DOUGLAS B. COMER

Attesting Officer     Acting Commissioner of Patents and Trademarks